United States Patent [19]

Thornthwaite

[11] Patent Number: 4,668,618

[45] Date of Patent: May 26, 1987

[54] NUCLEAR ISOLATION MEDIUM AND PROCEDURE FOR SEPARATING CELL NUCLEI

[76] Inventor: Jerry T. Thornthwaite, 117 Blakemore Cir., Johnson City, Tenn. 37601

[21] Appl. No.: 574,647

[22] Filed: Jan. 30, 1984

Related U.S. Application Data

[63] Continuation of Ser. No. 301,599, Sep. 14, 1981, abandoned, which is a continuation-in-part of Ser. No. 257,155, Apr. 24, 1981, abandoned.

[51] Int. Cl.[4] ............... C12Q 1/68; C12Q 1/02
[52] U.S. Cl. ....................................... 435/6; 435/29; 435/810; 435/259; 436/8; 436/17; 436/18; 436/63; 436/172; 436/175; 436/177
[58] Field of Search ............ 435/1, 6, 29, 30, 240, 435/241, 810, 820, 259; 436/8, 10, 17, 18, 63, 64, 813, 166, 172, 175, 177; 424/3

[56] References Cited

U.S. PATENT DOCUMENTS

| | | | |
|---|---|---|---|
| 3,684,377 | 8/1972 | Adams et al. | 250/461 B |
| 3,864,212 | 2/1975 | Berkhan | 435/6 |
| 3,883,247 | 5/1975 | Adams | 250/461 B |
| 4,061,537 | 12/1971 | Seiler | 435/1 |
| 4,102,810 | 7/1978 | Armstrong | 23/230 B |
| 4,286,963 | 9/1981 | Ledis et al. | 252/408 |
| 4,297,238 | 10/1981 | Vormbrock et al. | 23/230 B |
| 4,299,726 | 11/1981 | Crews et al. | 23/230 B |
| 4,303,752 | 12/1981 | Kolehmainen et al. | 435/18 |
| 4,319,882 | 3/1982 | Sharma | 23/230 B |

OTHER PUBLICATIONS

Taylor, J., Histochem. Cytochem., 28(9), 1021-1024, (1980).
Gray, *Methods in Enzymology*, vol. LVIII, Academic Press, New York, 233-247, (1979).
Thornthwaite et al, Cytometry, 1(3):229-237 (1980).

*Primary Examiner*—Esther M. Kepplinger
*Attorney, Agent, or Firm*—Cushman, Darby & Cushman

[57] ABSTRACT

Nuclear isolation media and procedures are described for dissociating discrete, non-agglomerated cell nuclei from animal tissue without the need to use enzyme treatments, centrifugation or the like in order to achieve the desired separation. The media facilitates separation and maintains the nuclear membrane intact and in its normal physiological environment. When a DNA-fluorochrome stain is included in the medium an essentially one step combination nuclear isolation and DNA staining procedure is used to measure DNA in tissue cells by flow cytometry. Rapid and consistent results are obtained and multiple sampling of the same tissue or comparison between whole tissues and their single cell isolates are also described.

21 Claims, No Drawings

NUCLEAR ISOLATION MEDIUM AND PROCEDURE FOR SEPARATING CELL NUCLEI

CROSS REFERENCE TO RELATED APPLICATIONS

This is a continuation of application Ser. No. 301,599, filed Sept. 14, 1981, now abandoned, which is a continuation-in-part of my earlier application Ser. No. 257,155 filed Apr. 24, 1981, now abandoned.

BACKGROUND OF THE INVENTION

This invention relates to the preparation of tissues for cytometric analysis and observation. More particularly a liquid medium is described for preparing animal tissues for automated or microscopic analysis in which the cell nuclei are separated into discrete, non-agglomerated units. The medium and procedure is specifically tailored for flow cytometry.

In order for flow cytometry to be useful in studies of the proliferation kinetics and carcinogenesis of mammalian cells, a consistent, rapid method is necessary for the preparation of single cells or nuclei suspensions from solid tissues. Much work has been accomplished utilizing ascites tumors, cell cultures and hemopoetic tumors. Since these samples comprise single cells, preparation for cytometric analysis is simply a matter of staining the cells for DNA content while avoiding cell clumping. Sample preparation of solid tumors or tissues for flow cytometric analysis, however, becomes much more difficult, since the cells must be separated from each other completely in order to minimize false DNA histograms generated by two or more cells adhering to one another.

There is generally no acceptable procedure for the disaggregation of cells from tissues. The ideal technique, therefore, must be determined by trial and error in which the best method of disaggregation is only applicable for a specific tissue in only one species. This problem is amplified in human tumor biopsy analysis. An added problem of scar tissue build-up due to either surgical or radiation therapies can cause inconsistent results in multiple biopsies of the same patient.

Several preparative methods have been used for the production of single cells. The most popular procedures have utilized enzymes with the goal of recovering viable cells which are representative of the whole tissue. Some of the enzymes which have been used include trypsin for murine squamous-cell carcinoma, pepsin for metastatic human tumors, and combinations of trypsin-collagenase; see Noel, J. S. et al, "The Dissociation of Transplantable Tumors", J. Histochem Cytochem 25:544 (1977). Other methods have applied nonenzymatic, chemical procedures or physical techniques with the main goal to recover a maximum number of single cells for flow cytometric studies.

In general, these preparative methods are multistep processes which require a customized treatment on each type of tissue under analysis to insure maximum dissociation. Thus there is the disadvantage that each procedure is tissue specific. Also, the reproducibility of the majority of these methods has not been firmly established. Furthermore, cell dissociation is not always complete, and the intepretations of flow cytometric DNA histograms are suspect because of cell aggregation creating false DNA values. These cell aggregates also make microscopic pattern recognition difficult in that the edge boundaries of aggregated cells cannot always be clearly defined.

If one is interested in quantitating nuclear DNA in a single cell, then nuclear isolation would be sufficient. The standard biochemical procedures for nuclear isolation from tissues usually require homogenization and centrifugation steps which have been found to lead to incomplete tissue dissociation, release of DNA from destroyed nuclei and clumping of centrifuged nuclei. These procedures are unacceptable for flow cytometric measurements. Hypotonic solutions, always used with single cell preparations but not tissue, without and with the nonionic surfactant, nonidet P 40 (NP40) have been used to isolate nuclei from single cells for flow cytometric DNA analysis with propidium iodide. A hypertonic saline solution with NP40 has been utilized to obtain nuclei from solid tumors; see Vindelov, "Flow Microfluorometric Analysis of Nuclear DNA In Cells From Solid Tumors And Cell Suspension"; Virchows Arch [Cell Pathol] 24:227 (1977).

The objective of the present invention is to provide a dependable, rapid method for isolating fluorochrome stained nuclei from normal and cancerous tissues. This one-step procedure of combination nuclear isolation and fluorochrome DNA staining does not require a centrifugation step, therefore, nuclear clumping is avoided. A wide range of tissues may be utilized.

Accordingly it is an object of the present invention to provide materials and methods for measuring DNA in tissue cells by flow cytometry utilizing a one step combination nuclear isolation-DNA fluorochrome staining medium and procedure. The advantages of this procedure are that the disclosed nuclear isolation medium (NIM) provides a simple, one step procedure that takes only 5–10 min. to obtain a representative sample. This allows for the preparation of multiple samples from the same tissue in order to define more accurately the characteristics of the whole tissue. Moreover, with easily dissociated tissues, one can compare the single cell and tissue nuclear isolates to see if their DNA distributions are equivalent. In the majority of samples, there is minimal sample debris which results in consistent, high resolution DNA histograms in the 1–2% coefficient of variation range regardless of the tissue analyzed. Finally, since the NIM is easily prepared and the disaggregation procedure is a single step process, the whole preparation technique can be standardized, thus allowing accurate comparison of data between laboratories.

Besides the DNA quantitation there are a number of useful parameters in the cell nucleus to which the present invention is well adapted. First of all, nuclear volume may be a useful parameter in characterizing tumor development as shown for erythroleukemic cells. Furthermore, one of the most important criteria for the detection, classification, and staging of tumor cells is nuclear area. For example, the mean nuclear area for cells in carcinoma in situ is about three times that of normal squamous cell nuclei. Endometrial adenocarcinoma nuclei show an increase in area which is directly proportional to the grading scale of these tumors. Also, there is a significant increase in nuclear area in ectocervical when compared to endocervical tumors.

By utilizing high resolution DNA fluorescent measurement with electronic nuclear volume, two parameter scattergrams can be generated in order to develop a fingerprint technique for the detection and classification of tumors. This correlative analysis would be especially useful in solid tumor studies where single cell preparations are difficult to obtain. In general, there are a number of antigens, receptors and enzymes that may be expressed in the nuclei. Certain histocompatability antigens are expressed in the nuclear membrane. Probably the most important site in the cell to look for estrogen and progesterone receptors is in the nucleus. Finally, there are several important enzymes in the nucleus. One of these is found in NIM isolated liver nuclei where 5'-ATPase levels increase significantly in tumor cells. These and other applications of the procedures of the present invention will be apparent to those skilled in the art.

DETAILED DESCRIPTION OF THE INVENTION

In its compositional aspect the present invention provides a nuclear isolation medium (sometimes referred to herein as NIM) for separating cell nuclei that consistently and rapidly allows the isolation of single cell nuclei by the disaggregation of cells from tissues. The medium is particularly adapted for use in human tumor biopsy analysis, although it is well suited for other cytological procedures for human and other animal tissue.

In order to isolate readily observable and/or analyzable discrete cell nuclei it is necessary to establish a medium that mirrors the external fluid of the tissue from which the cell nuclei are to be examined, i.e., the area about the cell in question, and to this end animal-to-animal and tissue-to-tissue variations exist. Thus while my invention will be described essentially with reference to studies of human-derived tissue, it will be understood that through suitable adjustments one may deal with other animal tissues as well. A medium hospitable to cell nuclei should necessarily have an ionic content comparable to the tonicity of the fluid external to the cell, i.e., a tonicity substantially similar or identical the area about the cell in question. Isotonicity is an essential requirement for the nuclear isolation media of my invention.

There are variations between various classes of animals—as an example the average ion content for media for use with human-derived cells is 146 mM Na and other ions or a disaccharide may be used. Typically sodium ion is the ion employed. Isotonicity has not been a characteristic of previously described nuclear isolation media for flow cytometric analysis.

In addition to sodium ion concentration "normal tonicity" is also relatable to red blood cells (erythrocytes) of the animal under study. Red blood cells are well recognized as an accurate osmometer. Although osmolarity and tonicity are not synonymous, a convenient standard to which to compare for nuclei are the whole erythrocytes of the animal from which the animal tissue sample is isolated.

As used herein the expression "normal electronic cell volume of the cell nuclei", in addition to or as an alternative of sodium ion concentration, includes a comparison with whole erythrocytes of the animal in question as a basis for establishing an isotonic solution. For such a comparison, an isotonic medium is established using the nuclear isolation medium as disclosed herein—absent the nonionic surfactant component—and using this solution comparing with the erythrocyte cell volume when these cells are suspended in the animal's natural peripheral blood fluid. When observed via electronic means the two electronic erythrocyte cell volume distributions appear substantially completely identical to the extent that the coefficient of variation (CV) between the two, expressed as a percentage and peak channel number, are both +2%. These measurements are described in more detail in Thornthwaite et al, "The Use of Electronic Cell Volume Analysis . . . ", Scanning Electron Microscopy (1978), Volume II, pp. 1123–1130, the disclosure of which is incorporated by reference.

A second essential ingredient of the nuclear isolation media is a minor amount of a nonionic surfactant. Suitable nonionic surfactants are described in McCutcheon's Detergents and Emulsifiers (1977). Preferred are Nonidet P 40, an octylphenol ethylene oxide condensate with an average of 9 moles of ethylene oxide available as a 27% solution from Accurate Scientific and Chemical Co., Triton X-100, an octylphenoxy polyethoxy ethanol available from Rohm & Haas, and Octy Glycoside, a 1-0-n-octyl-beta-d-glycopyranoside available from Sigma Chemical Co. A suitable surfactant is easily determined by empirical selection and evaluation.

The amount of surfactant included in the media should be sufficient that dissociation is nearly complete, that is there is less than 2% clumped nuclei when observed under a microscope, substantial numbers of clumped cell nuclei evidence incomplete cell dissolution. The desirable level is an amount that allows a smooth and even flow in DNA flow cytometric analysis equipment, as described more fully below. Excessive amounts of surfactant are evidenced by loss of cell integrity and swollen or shrunken cells. Surfactant quantity is also indicated by the intensity of the fluorescent stain when such stain is used. Excessive amounts of surfactant decreases the fluorescence of the stain to an unacceptable level.

As indicated, the preferred surfactant is Nonidet P 40 (available as a 27% by weight solution) which is included in the media within the range of about 0.1 to about 5% v/v and preferably in the range of about 0.6 to about 2% v/v.

Also a microscopy-type stain is usually included in the medium. Illustrative stains include protein stains, such as fluorescein isothiocyanate; RNA stains such as acridine orange; antibody stains; receptor binding compounds; and enzyme substrate stains. Preferred in flow cytometric analysis are the DNA fluorochrome-type stains such as 4',6-diamidino-2-phenylindole-2 HCl and propidium iodide. DNA stains for fluorescence and/or phosphorescence may also be used. The stain is included in an amount as is customarily used in cytometric procedures. Combinations of various stains may also be used.

An environment hospitable to the cell nuclei preferably also includes serum albumin in an amount selected to match that of the physiological state of the animal from which the tissue was taken. When used serum albumin is present in an amount of about 0.05 to about 1.0% and preferably in an amount of about 0.2%. Divalent cations, particularly calcium and magnesium, are included in the media as such ions have been found important in the preservation of the nuclear membrane; see R. Hancock, J. Cell Physiol 97:37 (1978).

The media should have a pH of about 5 to about 8 and preferably from about pH 6.5 to about pH 7.5. The specific pH will be selected to be equivalent to the physiological pH of the animal in question. A buffer or buffer system is also included in an optional ingredient to maintain the pH of the media.

In its procedural aspect the invention provides a convenient one-step method of preparing cells and tissue samples for cell nuclei observation and analysis using flow or static cytometric measurements. Maximum cell dissociation is achieved and cell aggregation is avoided in this procedure. A wide variety of tissues may be used, including frozen tissue, which when subjected to nuclear volume and DNA fluorescence flow cytometric analysis provides a marker for neoplastic cells.

A typical procedure includes placing 0.2 g of tissue under study in a petri dish, adding 3 ml. of the nuclear isolation media, described above, mincing the tissue with a sharp instrument and waiting 5 minutes. The tissue and liquid mixture are filtered through a 70 micron filter to remove cell debris. The nuclei, usually 10 to 15 microns in diameter, pass the filter and are collected in a vessel together with the passed liquid. Optionally the cells/liquid mixture is syringed or subjected to ultrasonication to assure single cell nuclei. The resulting preparation is complete and ready for static or flow cytometric analysis. It will be understood that this is but one of many dissociation procedures that may be employed; the skilled analytical worker will have no difficulty in achieving the desired degree of dissociation following the procedures herein described.

The invention will now be described with reference to the following example, considered illustrative but not limiting, the invention.

Tissue Sources:

A variety of tissues was used in this study. Sarcoma tumors were produced by 3-methylcholanthrene (MCA) induction in C57BL/6J, male mice. Their associated metastatic nodules were isolated from the lungs of mice who had their intramuscular induced tumor-bearing legs amputated. This decrease in tumor burden promoted metastatic growth. The following normal tissues were utilized from the C57BL/6J mice: liver, bone marrow and testicle. A murine brain tumor was prepared for flow cytometric analysis. Wistar rats were utilized as the source of pancreatic islets. Normal human samples included peripheral blood leukocytes and colon mucosa. Human tissue samples from biopsy specimens included colon, sarcoma and brain tumors.

Nuclear Isolation and Staining Technique:

Nuclear isolation and DNA fluorochrome staining were combined in a rapid, one step procedure. The nuclear isolation medium (NIM) consisted of 0.01 M phosphate buffered isotonic saline (146 mM) with calcium (1.0 mM $CaCl_2$) and magnesium (0.5 mM $MgSO_4.7\ H_2O$) which contained 0.6% NP40 (v/v) (Accurate Scientific and Chemical Co., Hicksville, N.Y.) and 0.2% bovine serum albumin (BSA) (w/v) (Fraction Five GIBCO). This formulation was developed after a series of studies with various physiologic buffers (pH 6.5–7.5) and different concentrations of the various components. The BSA was not an absolute requirement but did help stabilize the nuclear membranes. A commercially available phosphate buffer (0.01 M) saline (152 mM) with calcium and magnesium (Dulbecco, GIBCO) was similar in the NIM phosphate buffered saline solution and substituted very well for the above formulation.

The DNA fluorochrome 4'6-diamidino-2 phenylindole-2 HCl (DAPI) (Accurate Scientific and Chemical Co.) was dissolved in the nuclear isolation medium at a concentration of 10 g/ml. Tissues (0.1–0.3 g) were minced with scalpels in the NIM-DAPI stain solution (0.1 g/ml) for about 1–2 min. After mincing, the tissues were left in the NIM-DAPI for 3 min. at room temperature. The suspensions were then filtered through a 70- nylon mesh to remove tissue debris. The nuclei were syringed through a 26-gauge needle back and forth twice and filtered through the 70- mesh. This syringing procedure was used with all of the samples only as a precautionary measure to insure single nuclei, since the NIM step resulted in almost complete nuclear dissociation. The stained nuclear isolates were observed using a fluorescent microscope to determine the percentage of nuclear aggregates. If greater than 2% of the nuclei were joined together, they were syringed again. Samples not analyzed immediately were left at 4° C. for up to 48 hr. and then syringed and filtered before analysis. The dissociative activity of the NIM was stable for about 3 months if it was kept in the refrigerator.

Flow Cytometry:

An ICP-22 Flow Cytometer (Ortho Instruments, Westwood, Mass.) was interfaced to a SUE Lockheed computer (Lockheed Electronics, Plainfield, NJ). With this system, the measurement, acquisition and analysis of the DNA content of isolated nuclei was accomplished. DAPI fluorescence was quantitated utilizing a BG 1 exciter filter, a TK 405 dichroic and LP 395 barrier filter. The nuclei were analyzed at a rate of 300–400 nuclei/sec. In cases where the Coulter Epics-IV cell sorter (Coulter Electronics, Hialeah, FL) was utilized, propidium iodide (Calbiochem) was substituted for DAPI in the NIM at a concentration of 50 g/ml.

Fluorescence Photomicroscopy:

A Zeiss Photomicroscope III with a 100 watt mercury lamp was used in photographing the DAPI stained nuclei. A BG 3 exciter filter was used with an additional cut-off filter to isolate the mercury line range around 405 nm. The blue-green fluorescence was isolated utilizing a dichroic beam splitter and LP 475 barrier filter.

For cell populations which can be teased into single cell suspensions, for example, bone marrow, lymphoid organs and peripheral blood, the media and technique of the present invention is not necessary if a DNA specific stain, such as DAPI, is utilized. NIM is required in cases where one utilizes an intercalating dye, such as propidium iodide which will bind with RNA as well as DNA. By isolating nuclei, the staining by cytoplasmic RNA is eliminated.

The procedures and media of this invention are useful not only in preparing tissues for flow cytometric analysis, for instance in determining S phase DNA synthesis, but also in tumor detection and radiation or chemotherapy monitoring. A detailed discussion of specific adaptations for flow analysis, observations and other evidence of performance is contained in Thornthwaite et al, "Preparation of Tissues for DNA Flow Cytometric Analysis", Cytometry, Volume 1, No. 3, pp. 229–237 (1980) the disclosure of which is hereby incorporated by reference. The technique of and equipment for flow analysis is described in the text Flow Cytometry and Sorting, Melamed, et al, editors, John Wiley & Sons (1979).

Another use for the media of the present invention is to remove intact nuclei from a tissue culture plate. Previous procedures employed various enzyme-containing solutions which released the cells from the tissue culture plate and also altered the condition of the nuclei so released. Using the nuclear isolation media described above the cell nuclei came loose from the tissue culture plate in a single step.

The tissue sources are maintained at about room temperature or frozen tissues, i.e. −80° C., may be conveniently used.

The nuclear isolation technique is useful to compare normal cell nuclei with suspected cell nuclei as in DNA flow cytometric analysis in order to establish "normal" amounts of DNA in normal tissue and thus compare this with suspected tissue of the same histological type. Prior procedures required a standardization step with "normal" single cells, such as white blood cells. This was then compared with the cell nuclei of the suspected tissue, which in all cases except white blood cells was of a different tissue type. Using the procedure of the invention it is now possible to dissociate nuclei of the same histological type tissue for both normal and "abnormal" tissue. Thus a bank of stock tissues may be retained, and frozen, i.e. about −80° C. if desired, and made available to compare and cross-analyze with suspected cells of the same histological tissue type.

The nuclear isolation media of the present invention is capable of lysing red blood cells. This is a useful property, particularly when preparing whole blood for analytical cytology. The nuclear isolation media lyses and helps to remove red cells, which contain no DNA, leaving the white cell DNA nuceli intact for study and analysis in a single step. Previous procedures required an enzymatic red cell lysis step.

What is claimed is:

1. A nuclear isolation medium for DNA flow cytometric analysis used to dissociate an animal tissue sample into discrete, non-agglomerated cell nuclei, said medium consisting essentially of
    a nonionic surfactant present in an amount sufficient to separate the cell nuclei while maintaining nuclear membrane integrity;
    a microscopy stain for staining the DNA cell content;
    serum albumin in an amount substantially the same as the physiological state of the tissue sample; and
    divalent cations in an amount substantially equal to the amounts of said cations in the fluid surrounding the nuclear membrane of the tissue sample, dissolved in an aqueous solution that is substantially completely isotonic with and maintains the normal electronic volume of the cell nuclei, the medium having a pH that is in the range of pH 6.5 to 7.5 and is substantially identical to the physiological pH of the animal from which the tissue originates.

2. The nuclear isolation medium of claim 1 wherein the divalent cations are magnesium and/or calcium and the serum albumin concentration is about 0.05% to 1.0% v/v.

3. The nuclear isolation medium of claim 1 wherein the sodium ion concentration is about 146 mM Na+.

4. Discrete, non-agglomerated cell nuclei contained in the nuclear isolation medium of claim 1.

5. A method of dissociating cell nuclei from an animal tissue containing same into discrete, nonagglomerated individual cell nuclei, said method comprising the steps of:
    (a) placing a tissue sample in a nuclear isolation medium containing an isotonic solution of a cell-separating amount of a nonionic surfactant and at least one microscopy stain;
    (b) physically mincing the tissue sample while in contact with the nuclear isolation medium;
    (c) allowing the minced tissue sample to remain in contact with the nuclear isolation medium until a quantity of single nuclei have been separated; and
    (d) removing the single nuclei from the remaining tissue and cellular debris.

6. The cell nuclei dissociation method of claim 5 wherein the nuclear isolation medium is buffered.

7. The cell nuclei dissociation method of claim 5 wherein the nuclear isolation medium also contains serum albumin in an amount substantially the same as the physiological state of the animal from which the tissue was taken.

8. The cell nuclei dissociation method of claim 5 wherein the serum albumin is present in an amount of from about 0.05% to about 1.0% by weight.

9. The cell nuclei dissociation method of claim 5 wherein the nuclear isolation medium also contains divalent cations in an amount substantially equal to the amounts of said cations in the fluid surrounding the nuclear membrane of the tissue sample.

10. The cell nuclei dissociation method of claim 5 wherein the divalent cations are calcium, magnesium or their mixtures.

11. The cell nuclei dissociation method of claim 9 wherein the nuclear isolation medium also contains:
    serum albumin in an amount substantially the same as the physiological state of the animal from which the tissue was taken, and
    magnesium plus calcium ions in amounts substantially equal to the amounts of said cations in the fluid surrounding the nuclear membrane of the tissue sample.

12. The cell nuclei dissociation method of claim 6 wherein the single cell nuclei are removed from the tissue and cellular debris in step (d) by filtration.

13. The cell nuclei dissociation method of claim 5 including the additional step of:
    (e) subjecting the separated nuclei to DNA flow cytometric analysis.

14. A method of preparing tissue for DNA flow cytometric analysis by dissociating cell nuclei from an animal tissue containing same into discrete, non-agglomerated individual cell nuclei, said method comprising the steps of:
    (a) placing a tissue sample in a nuclear isolation medium containing a solution of a cell-separating amount of a nonionic surfactant and a DNA stain in a buffered aqueous solution that is substantially isotonic with and maintains the normal electronic volume of the cell nuclei, said medium having a pH in the range of 5 to 8 and substantially the same as the physiological pH of the animal from which the tissue originates;
    (b) physically mincing the tissue sample while in contact with the nuclear isolation medium;
    (c) allowing the minced tissue sample to remain in contact with the nuclear isolation medium until at least an analyzable quantity of single nuclei have been separated;
    (d) filtering and removing the single nuclei from the tissue and cellular debris, and
    (e) subjecting the thus separated nuclei to DNA flow cytometric analysis.

15. The method of claim 14 wherein the nuclear isolation medium also contains serum albumin in an amount substantially the same as the physiological state of the animal from which the tissue was taken.

16. The method of claim 15 wherein the nuclear isolation medium additionally contains magnesium and/or calcium ions in an amount substantially equal to the amounts of said ions in the fluid surrounding the nuclear membrane of the tissue sample.

17. The method of comparing normal cell nuclei with suspended cell nuclei both said nuclei of the same histological type, said method comprising the steps of:
(1) placing a normal tissue sample in a nuclear isolation medium composed of a cell nucleus-separating amount of a nonionic surfactant and a fluorescent, phosphorescent, or absorbance stain, the surfactant and stain contained in a buffered aqueous solution that is substantially isotonic with the cell nuclei and has a pH (a) in the range of 5 to 8, and (b) is substantially the same as the physiological pH of the animal from which the tissue was taken,
and separating a first group of single nuclei from the remaining normal tissue and cellular debris;
(2) placing a suspected tissue sample in said nuclear isolation medium and separating a second group of single nuclei from the remaining suspected tissue and cellular debris; and
(3) comparing the first group of single nuclei with the second group of nuclei.

18. The comparison method of claim 17 wherein the groups of cell nuclei are compared by analytical cytology analysis in step (3).

19. The comparison method of claim 17 wherein the nuclear isolation medium also contains serum albumin in an amount substantially the same as the physiological state of the animal from which the samples were taken.

20. The method of claim 19 wherein the nuclear isolation medium additionally contains magnesium and/or calcium ions in an amount substantially equal to the amounts of said ions in the fluid surrounding the nuclear membrane of the tissue sample.

21. The comparison method of claim 17 wherein the normal tissue sample is taken from one individual and the suspected tissue sample is taken from a second individual.

* * * * *